United States Patent [19]

Eriksson

[11] Patent Number: 5,510,702
[45] Date of Patent: Apr. 23, 1996

[54] METHOD AND APPARATUS FOR SIMULTANEOUS MEASURING THE STREAMING POTENTIAL OF A FIBER SUSPENSION AND A FILTRATE THEREOF

[75] Inventor: Rune Eriksson, Mariestad, Sweden

[73] Assignee: AB Innomatic, Mariestad, Sweden

[21] Appl. No.: 352,027

[22] Filed: Nov. 30, 1994

[30] Foreign Application Priority Data

Dec. 2, 1993 [SE] Sweden .................................. 9304006

[51] Int. Cl.$^6$ ........................... G01N 27/00; G01N 11/02
[52] U.S. Cl. ..................... 324/71.1; 324/448; 324/450; 73/53.04
[58] Field of Search .................................. 324/71.1, 439, 324/448, 450, 713; 73/53.03, 53.04; 162/198, 263

[56] References Cited

U.S. PATENT DOCUMENTS

| | | | |
|---|---|---|---|
| 2,602,325 | 7/1952 | Campbell et al. | 73/53.04 X |
| 3,538,749 | 11/1970 | Danworth | 73/53.04 |
| 4,535,285 | 8/1985 | Evans et al. | 324/71.1 |
| 4,687,986 | 8/1987 | Eriksson | 324/71.1 |
| 5,365,775 | 11/1994 | Penniman | 324/71.1 X |
| 5,373,229 | 12/1994 | Penniman | 324/71.1 |

Primary Examiner—Kenneth A. Wieder
Assistant Examiner—Diep Do
Attorney, Agent, or Firm—Dennison, Meserole, Pollack & Scheiner

[57] ABSTRACT

A method and apparatus for simultaneously measuring the streaming potential of a fiber suspension and a filtrate thereof. A container is provided having an inlet and an outlet for the flow of fiber suspension therethrough, and a filter screen divides the container into an upstream compartment and a downstream compartment. Each compartment has an electrode pair disposed therein, each electrode pair including a cylindrical outer electrode configured for flow of fiber suspension therethrough and an inner electrode. Each electrode pair is connected to a differential amplifier, with the differential amplifiers connected to a microprocessor.

5 Claims, 1 Drawing Sheet

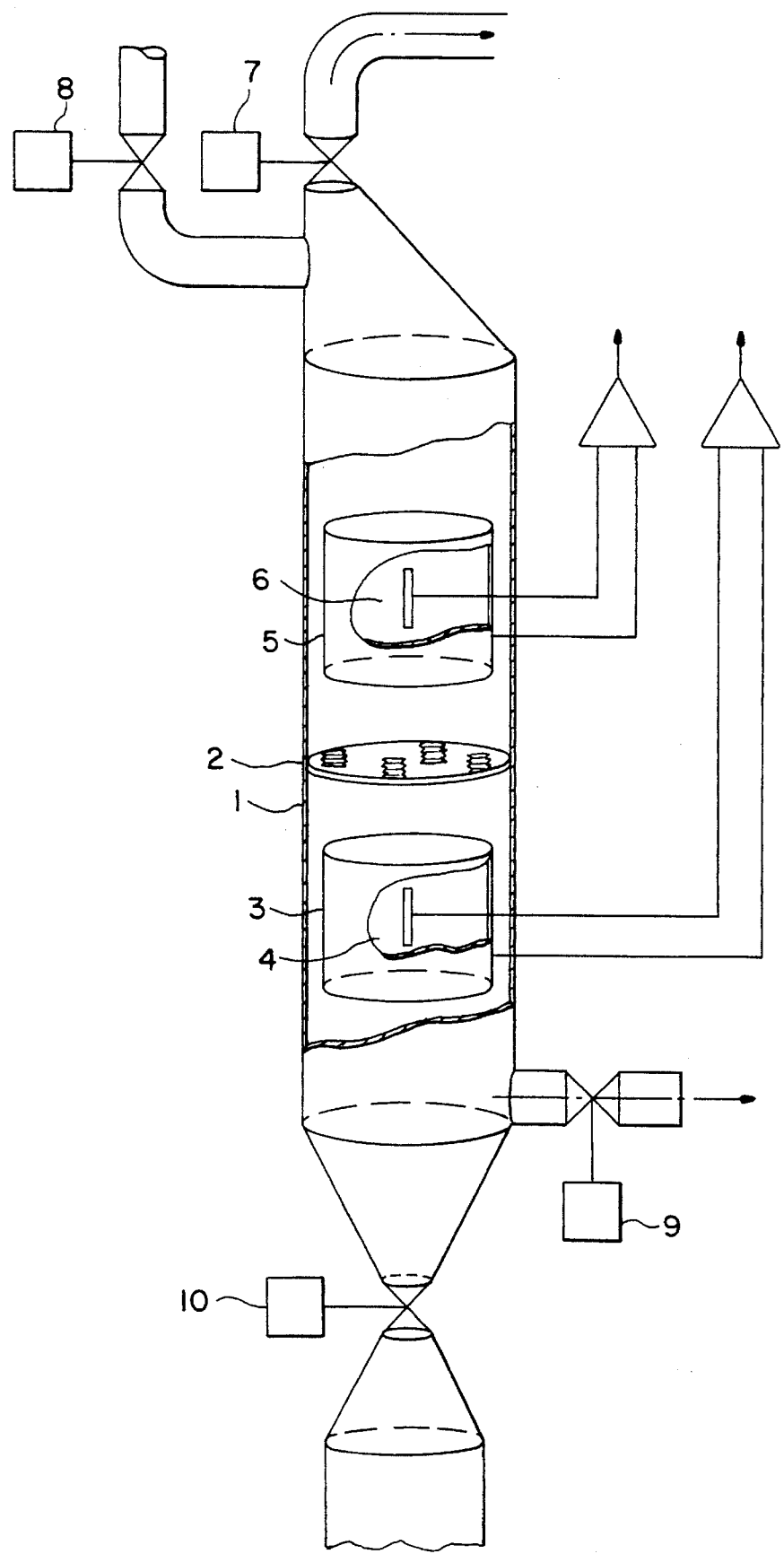

METHOD AND APPARATUS FOR SIMULTANEOUS MEASURING THE STREAMING POTENTIAL OF A FIBER SUSPENSION AND A FILTRATE THEREOF

BACKGROUND OF THE INVENTION

In streaming fiber suspensions, e.g. suspensions of pulp for paper production low electrical charges are developed. It is of great importance for the efficiency for the paper production as well as for the efficiency of the sewage system that this streaming potential can be measured and controlled continuously.

U.S. Pat. No. 4,687,986 describes a method for continuously measuring the streaming potential in an industrial process. The measurement is carried out across a screen, which removes the fibers in the sample by filtration and the values are processed in a microcomputer.

SUMMARY OF THE INVENTION

The present invention has for its purpose the provision of an apparatus for simultaneous measurement of the streaming potential in a fiber suspension and in its filtrate. This has not been possible in prior art. Such a simultaneous measurement is very advantageous for the control of the electric charge of the fiber stock.

BRIEF DESCRIPTION OF THE DRAWING

The sole drawing FIGURE is a schematic view, in partial cross-section, of an embodiment of the apparatus according to the invention.

DESCRIPTION OF THE PREFERRED EMBODIMENTS

The apparatus comprises a measuring vessel 1 with screenplate 2 and with two pairs of electrodes 3, 4 and 5, 6, the electrodes 4 and 6 being located inside the electrodes 3 and 5. The electrodes are made of the same material, preferably stainless steel. Each electrode is connected to its own differential amplifier, 11 or 12. The differential amplifiers are connected to a microprocessor 13. The pairs of electrodes are located on each side of the screen plate 2, which is kept under pressure on the side of the fibersuspension. On the filtrate side of the screen plate 2 there is a valve 7 provided on the filtrate side of the screen plate 2. The valve 7 can be opened and closed to the atmosphere in order to give a pulsating pressure over the screen plate 2. The apparatus also has valves 8, 9 and 10.

When measuring the fiber suspension is introduced through the valve 10 and is filtered with the screen plate 2. The measurement is carried out simultaneously on the fiber suspension and on the filtrate. During the measurement a pulsating pressure is formed over the screen plate, as the valve 7 is alternatively opened and closed to the atmosphere. Owing to this a pulsating electrical voltage is generated over the electrodes. Via the differential amplifiers this voltage is fed to a microprocessor for processing. The screen 2 can be cleaned from fibers by blowing with air through the valves 8 and 9, while the valves 7 and 10 are closed. The apparatus functions in a satisfactory way in spite of the fact that the measured voltages are very weak and that there is a great risk for disturbances in a factory environment.

I claim:

1. An apparatus for simultaneously measuring the streaming potential of a fiber suspension and a filtrate thereof, comprising a container having an inlet and an outlet for flow of fiber suspension therethrough, a filter screen dividing the container into an upstream compartment and a downstream compartment, a first electrode pair disposed in the upstream compartment comprising a first generally cylindrical outer electrode configured for flow of fiber suspension therethrough and a first inner electrode centrally disposed within the first outer electrode, a second electrode pair disposed in the downstream compartment comprising a second generally cylindrical outer electrode configured for flow of fiber suspension therethrough and a second inner electrode centrally disposed within the second outer electrode, a first differential amplifier connected to the first outer electrode and the first inner electrode for measuring potential difference therebetween, a second differential amplifier connected to the second outer electrode and the second inner electrode for measuring potential difference therebetween, a microprocessor connected to outputs from the first and second differential amplifiers, a valve disposed at the outlet for venting to the atmosphere and means for opening and closing the valve.

2. Apparatus according to claim 1, additionally comprising an air inlet at the outlet of the container and an air outlet at the inlet of the container for cleaning the filter screen.

3. A method for simultaneously measuring the streaming potential of a fiber suspension and a filtrate thereof, comprising the steps of:

a) causing the fiber suspension to flow through a filter screen to produce a filtrate downstream of the filter screen;

b) opening and closing a valve to the atmosphere downstream of the filter screen to generate a pulsating pressure on the filter screen, and thereby to cause a pulsating voltage;

c) measuring upstream of the filter screen a first differential voltage perpendicular to the direction of flow of the fiber suspension;

d) measuring downstream of the filter screen and upstream of the valve a second differential voltage perpendicular to the direction of flow of the fiber suspension; and e) comparing the first and second differential voltages.

4. A method for simultaneously measuring the streaming potential of a fiber suspension and a filtrate thereof, comprising the steps of:

a) causing the fiber suspension to flow through a container divided into upstream and downstream compartments by a filter screen;

b) measuring a first differential voltage upstream of the filter screen perpendicular to the direction of flow of the fiber suspension with a first electrode pair comprising a first generally cylindrical outer electrode and a first inner electrode, the flow of the fiber suspension passing through the first outer electrode, said first outer electrode and said first inner electrode connected to a first differential amplifier;

c) measuring a second differential voltage downstream of the filter screen perpendicular to the direction of flow of the fiber suspension with a second electrode pair comprising a second generally cylindrical outer electrode and a second inner electrode, the flow of the fiber suspension passing through the second outer electrode, said second outer electrode and said second inner electrode connected to a second differential amplifier;

d) opening and closing a valve to the atmosphere downstream of the downstream compartment to generate a pulsating pressure on the filter screen, and thereby to cause a pulsating voltage; and
e) comparing the first and second differential voltages with a microprocessor.

5. Method according to claim 4, additionally comprising cleaning the filter screen by blowing air from an inlet in the downstream compartment to an outlet in the upstream compartment.

* * * * *